(12) United States Patent
Gordon et al.

(10) Patent No.: US 6,365,190 B1
(45) Date of Patent: *Apr. 2, 2002

(54) SYSTEMS AND PROCESSES FOR SPRAY DRYING HYDROPHOBIC DRUGS WITH HYDROPHILIC EXCIPIENTS

(75) Inventors: Marc S. Gordon, Sunnyvale; Andrew Clark, Half Moon Bay; Thomas K. Brewer, Walnut Creek, all of CA (US)

(73) Assignee: Inhale Therapeutic Systems, Inc., Sna Carlos, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/528,758

(22) Filed: Mar. 17, 2000

Related U.S. Application Data

(63) Continuation of application No. 08/999,097, filed on Dec. 29, 1997, now Pat. No. 6,077,543.
(60) Provisional application No. 60/034,837, filed on Dec. 31, 1996.

(51) Int. Cl.[7] .............................. A61K 9/14; A61K 9/72
(52) U.S. Cl. .................... 424/489; 424/45; 424/499; 424/502; 264/5; 264/7; 264/12; 264/13; 514/938; 514/958; 514/251
(58) Field of Search .................... 424/45, 46, 489, 424/499, 502; 514/938, 958, 251; 264/5, 7, 12, 13

(56) References Cited

U.S. PATENT DOCUMENTS

| | | | |
|---|---|---|---|
| 4,486,435 A | | 12/1984 | Schmidt et al. |
| 4,540,602 A | * | 9/1985 | Motoyama et al. ..... 427/213.31 |
| 4,590,206 A | * | 5/1986 | Forrester et al. ............ 514/456 |
| 4,670,419 A | | 6/1987 | Uda et al. |
| 4,898,781 A | * | 2/1990 | Onouchi et al. ............ 428/402 |
| 4,999,189 A | | 3/1991 | Kogan et al. |
| 5,000,888 A | | 3/1991 | Kilbride, Jr. et al. |
| 5,026,550 A | | 6/1991 | Aeschbach et al. |
| 5,260,306 A | | 11/1993 | Boardman et al. |
| 5,376,386 A | | 12/1994 | Ganderton et al. |
| 5,510,118 A | * | 4/1996 | Bosch et al. ................ 424/489 |
| 5,518,187 A | | 5/1996 | Bruno et al. |
| 5,534,270 A | | 7/1996 | De Castro |

(List continued on next page.)

FOREIGN PATENT DOCUMENTS

| | | |
|---|---|---|
| EP | 0611567 | 8/1994 |
| EP | 0655237 | 5/1995 |
| WO | WO 91/16882 | 11/1991 |
| WO | WO 94/07514 | 4/1994 |
| WO | WO 95/23613 | 9/1995 |
| WO | WO 95/24183 | 9/1995 |
| WO | WO 96/09814 | 4/1996 |
| WO | WO 97/36574 | 10/1997 |
| WO | WO 88/07870 | 10/1998 |

OTHER PUBLICATIONS

Bloch et al., "Dispersions of hydrochlorothiazide and chlorhalidone in pentaerythritol," *Pharm. Acta. Helv.* (1983) 58(1):14–22. An English abstract is also enclosed herewith.

Dialog® Abstract of German Patent Publication No. DE2209477. One page total.

Dialog® Abstract of French Patent Publication No. FR2594693. One page total.

(List continued on next page.)

*Primary Examiner*—Thurman K. Page
*Assistant Examiner*—Lakshmi Channavajjala
(74) *Attorney, Agent, or Firm*—Michael J. Rafa; Felissa H. Cagan

(57) ABSTRACT

Methods for preparing dry powders having hydrophobic and hydrophilic components comprise combining solutions of the components and spray drying them simultaneously in a spray dryer. The hydrophilic and hydrophobic component are separately dissolved in separate solvents and directed simultaneously through a nozzle, usually a coaxial nozzle, into the spray dryer. The method provides dry powders having relatively uniform characteristics.

18 Claims, 3 Drawing Sheets

U.S. PATENT DOCUMENTS

| | | | | |
|---|---|---|---|---|
| 5,667,806 A | * | 9/1997 | Kantor | 424/484 |
| 5,874,064 A | | 2/1999 | Edwards et al. | |
| 5,976,574 A | * | 11/1999 | Gordon | 424/489 |
| 5,985,248 A | * | 11/1999 | Gordon et al. | 424/46 |
| 6,001,336 A | * | 12/1999 | Gordon | 424/46 |
| 6,077,543 A | * | 6/2000 | Gordon et al. | 424/489 |

OTHER PUBLICATIONS

Dialog® Abstract of Japanese Patent Publication No. JP4036233. One page total.

Dialog® Abstract of Japanese Patent Publication No. JP7101881. One page total.

Dialog® Abstract of Japanese Patent Publication No. JP7101883. One page total.

Dialog® Abstract of Japanese Patent Publication No. JP7101884. One page total.

Dialog® Abstract of Japanese Patent Publication No. JP7101882. One page total.

Dialog® Abstract of Japanese Patent Publication No. JP7242568. One page total.

Dialog® Abstract of Japanese Patent Publication No. JP8067666. One page total.

Mumenthaler et al., "Feasibility study on spray–drying protein pharmaceuticals: Recombinant human growth hormome and tissue–type plasminogen activator," *Pharm. Res.* (1994) 11(1):12–20.

* cited by examiner

SYSTEMS AND PROCESSES FOR SPRAY DRYING HYDROPHOBIC DRUGS WITH HYDROPHILIC EXCIPIENTS

This application claims benefit of Provisional Application No. 60/034,837, filed on Dec. 31, 1996, the full disclosure of which is incorporated herein by reference, and is a continuation of Ser. No. 08/999,097, filed Dec. 29, 1997, now U.S. Pat. No. 6,077,543.

BACKGROUND OF THE INVENTION

1. Field of the Invention

The present invention relates generally to dry powder compositions and methods for their preparation and use. In particular, the present invention relates to methods for spray drying pharmaceutical and other compositions comprising a hydrophobic drug or other component and a hydrophilic excipient or other component.

Over the years, certain drugs have been sold in formulations suitable for oral inhalation (pulmonary delivery) to treat various conditions in humans. Such pulmonary drug delivery formulations are designed to be inhaled by the patient so that the active drug within the dispersion reaches the lung. It has been found that certain drugs delivered to the lung are readily absorbed through the alveolar region directly into blood circulation. Such pulmonary delivery can be effective both for systemic delivery and for localized delivery to treat diseases of the lungs.

Pulmonary drug delivery can itself be achieved by different approaches, including liquid nebulizers, aerosol-based metered dose inhalers (MDI's), and dry powder dispersion devices. Aerosol-based MDI's are losing favor because they rely on the use of chlorofluorocarbons (CFC's), which are being banned because of their adverse effect on the ozone layer. Dry powder dispersion devices, which do not rely on CFC aerosol technology, are promising for delivering drugs that may be readily formulated as dry powders.

The ability to deliver pharmaceutical compositions as dry powders, however, is problematic in certain respects. The dosage of many pharmaceutical compositions is often critical, so it is desirable that dry powder delivery systems be able to accurately, precisely, and reliably deliver the intended amount of drug. Moreover, many pharmaceutical compositions are quite expensive. Thus, the ability to efficiently formulate, process, package, and deliver the dry powders with a minimal loss of drug is critical. With dry powder drug delivery, both the delivered dose efficiency, i.e. the percentage of drug from a unit dose receptacle which is aerosolized and delivered from a delivery device, and the median particle size distribution, i.e. the deviation from the median size, are critical to the successful delivery of powders to a patient's lungs.

A particularly promising approach for the pulmonary delivery of dry powder drugs utilizes a hand-held device with a hand pump for providing a source of pressurized gas. The pressurized gas is abruptly released through a powder dispersion device, such as a venturi nozzle, and the dispersed powder made available for patient inhalation. While advantageous in many respects, such hand-held devices are problematic in a number of other respects. The particles being delivered are usually less than 5 $\mu$m in size, making powder handling and dispersion more difficult than with larger particles. The problems are exacerbated by the relatively small volumes of pressurized gas, which are available using hand-actuated pumps. In particular, venturi dispersion devices are unsuitable for difficult-to-disperse powders when only small volumes of pressurized gas are available with the handpump. Another requirement for hand-held and other powder delivery devices is efficiency. High device efficiency in delivering the drug to the patient with the optimal size distribution for pulmonary delivery is essential for a commercially viable product.

Spray drying is a conventional chemical processing unit operation used to produce dry particulate solids from a variety of liquid and slurry starting materials. The use of spray drying for the formulation of dry powder pharmaceuticals is known, but has usually been limited to spray drying of hydrophilic drugs in aqueous solutions, usually in combination with hydrophilic excipients. Many drugs, however, are hydrophobic, preventing spray drying in aqueous solutions. While spray drying of hydrophobic materials can often be accomplished using an organic solvent, the use of such non-aqueous solvents generally limits the ability to simultaneously spray dry a hydrophilic excipient.

For these reasons, it would be desirable to provide improved methods for spray drying pharmaceutical and other compositions which comprise both hydrophobic and hydrophilic components, such as hydrophobic drugs and hydrophilic excipients. Such spray drying methods should be compatible with a wide variety of hydrophobic drugs as well as conventional hydrophilic excipients, such as povidone (polyvinylpyrrolidone) and other water soluble polymers, citric acid, mannitol, pectin and other water soluble carbohydrates, and particularly with those excipients which are accepted for use in inhalation formulations, such as lactose, sodium chloride, and sodium citrate. Such spray drying methods will preferably produce particles having a uniform size distribution, with a mean particle size below 10 $\mu$m, preferably below 5 $\mu$m, and a standard deviation less than or equal to ±2 $\mu$m. Such powders should further exhibit uniform composition from batch to batch so that any tendency for particles of different compositions and/or sizes to separate in the lungs will have a reproducible impact on the therapeutic effect. Additionally, such spray drying methods should provide for dry powders which are physically and chemically stable and which have low levels of any residual organic solvents or other components which might be used in the spray drying process. At least some of the above objectives will be met by the various embodiments of the present invention which are described in detail below.

2. Description of the Background Art

Methods for spray drying hydrophobic and other drugs and components are described in U.S. Pat. Nos. 5,000,888; 5,026,550; 4,670,419, 4,540,602; and 4,486,435. Bloch and Speison (1983) Pharm. Acta Helv 58:14–22 teaches spray drying of hydrochlorothiazide and chlorthalidone (lipophilic drugs) and a hydrophilic adjuvant (pentaerythritol) in azeotropic solvents of dioxane-water and 2-ethoxyethanol-water. A number of Japanese Patent application Abstracts relate to spray drying of hydrophilic-hydrophobic product combinations, including JP 806766; JP 7242568; JP 7101884; JP 7101883; JP 71018982; JP 7101881; and JP 4036233. Other foreign patent publications relevant to spray drying hydrophilic-hydrophobic product combinations include FR 2594693; DE 2209477; and WO 88/07870.

WO 96/09814 describes spray dried pharmaceutical powders. In particular, Example 7 describes spray drying budesonide and lactose in ethanol where the budesonide is partially soluble and the lactose is insoluble. U.S. Pat. Nos. 5,260,306; 4,590,206; GB 2 105 189; and EP 072 046 describe a method for spray drying nedocromil sodium to form small particles preferably in the range from 2 to 15 μm for pulmonary delivery. U.S. Pat. No. 5,376,386, describes the preparation of particulate polysaccharide carriers for pulmonary drug delivery, where the carriers comprise particles sized from 5 to 1000 μm. Mumenthaler et al. (1994) *Pharm. Res.* 11:12 describes recombinant human growth hormone and recombinant tissue-type plasminogen activator. WO 95/23613 describes preparing an inhalation powder of DNase by spray drying using laboratory-scale equipment. WO 91/16882 describes a method for spray drying proteins and other drugs in liposome carriers.

The following applications assigned to the assignee of the present application each describe that spray drying may be used to prepare dry powders of biological macromolecules; application serial no. 08/644,681, filed on May 8, 1996, which was a continuation-in-part of application Ser. No. 08/423,515, filed on Apr. 14, 1995; application Ser. No. 08/383,475, which was a continuation-in-part of application Ser. No. 08/207,472, filed on Mar. 7, 1994; application Ser. No. 08/472,563, filed on Apr. 14, 1995, which was a continuation-in-part of application Ser. No. 08/417,507, filed on Apr. 4, 1995, now abandoned, which was a continuation of application no. 08/044,358, filed on Apr. 7, 1993, now abandoned; application Ser. No. 08/232,849, filed on Apr. 25, 1994, which was a continuation of application Ser. No. 07/953,397, now abandoned. WO 94/07514 claims priority from Ser. No. 07/953,397. WO 95/24183 claims priority from Ser. Nos. 08/207,472 and 08/383,475.

SUMMARY OF THE INVENTION

According to the present invention, methods for spray drying hydrophobic drugs and other materials are provided which overcome at least some of the deficiencies noted above with respect to prior spray drying processes. In particular, the spray drying methods of the present invention permit the simultaneous spray drying of the hydrophobic component with a hydrophilic component, such as a hydrophilic pharmaceutical excipient, under conditions which result in a dry powder comprising mixtures of both the hydrophilic and hydrophobic components. Although the methods of the present invention are particularly useful for forming pharmaceutical compositions where the hydrophobic component is a hydrophobic drug, usually present at from 0.01% to 95% of the powder, and the hydrophilic component is a hydrophilic excipient, usually present at from 99.99% to 5% of the powder, the methods may be applied more broadly to form dry powders comprising a variety of hydrophobic and hydrophilic components at different concentration ranges, including hydrophilic drugs and hydrophobic excipients.

The spray drying methods of the present invention are compatible with at least most hydrophilic pharmaceutical excipients, particularly including mannitol, povidone, pectin, lactose, sodium chloride, and sodium citrate. Use of the latter three excipients is particularly preferred for powders intended for pulmonary delivery as they are "generally recognized as safe" (GRAS) for such applications. The methods are also suitable for use with numerous hydrophobic drugs and nutrients, including steroids and their salts, such as budesonide, testosterone, progesterone, estrogen, flunisolide, triamcinolone, beclomethasone, betamethasone; dexamethasone, fluticasone, methylprednisolone, prednisone, hydrocortisone, and the like; peptides, such as cyclosporin and other water insoluble peptides; retinoids, such as all-cis retinoic acid, 13-trans retinoic acid, and other vitamin A and beta carotene derivatives; vitamins D, E, and K and water insoluble precursors and derivatives thereof; prostaglandins and leukotrienes and their activators and inhibitors including prostacyclin (epoprostanol), and prostaglandins $E_1$ $E_2$; tetrahydrocannabinol; lung surfactant lipids; lipid soluble antioxidants; hydrophobic antibiotics and chemotherapeutic drugs such as amphotericin B, adriamycin, and the like.

The spray drying methods can produce a uniform particle size distribution. For example, the mean particle diameter can be controlled below 10 μm, preferably below 5 μm, with a size distribution (standard deviation) less than ±2 μm. The particles of the powders so produced have a minimum batch-to-batch variability in composition, and are physically and chemically stable. The powders have minimum residual organic solvents to the extent they may have been used in the spray drying process.

In particular, the method of the present invention comprises preparing an aqueous solution of a hydrophilic component and an organic solution of a hydrophobic component in an organic solvent. The aqueous solution and the organic solution are simultaneously spray dried to form particles comprising a mixture of the hydrophilic and hydrophobic components. Usually the hydrophilic component has a concentration in the aqueous solution from 1 mg/ml to 100 mg/ml, preferably from 5 mg/ml to 60 mg/ml. The hydrophobic component has a solubility in the organic solution of at least 0.01 mg/ml, preferably at least 0.05 mg/ml. The concentration of the hydrophobic component in the organic solution is usually in the range from 0.01 mg/ml to 10 mg/ml, preferably from 0.05 mg/ml to 5 mg/ml. Preferred organic solvents include alcohols, ketones, ethers, aldehydes, hydrocarbons, and polar aprotic solvents, and the like and mixtures thereof. The use of a separate aqueous and organic solution to carry the hydrophilic and hydrophobic components, respectively, is advantageous in that it allows a much broader range of selection for the organic solvent, since the organic solvent does not also have to solubilize the hydrophilic component. It is also particularly advantageous for spray drying hydrophobic components and hydrophilic components which are chemically or physically incompatible in solution, since the solutions of the hydrophobic components and hydrophilic components do not reside together until they are passing through the spray nozzle during spray drying. This severely minimizes the contact time between the two solutions before drying occurs, and hence minimizes the potential for undesirable reactions to occur. Usually, the aqueous solution and organic solution will be spray dried through a common spray nozzle, more usually through a coaxial spray nozzle.

Powders prepared by any of the above methods will be collected from the spray dryer in a conventional manner for subsequent use. For use as pharmaceuticals and other purposes, it will frequently be desirable to disrupt any agglomerates which may have formed by screening or other conventional techniques. For pharmaceutical uses, the dry powder formulations will usually be measured into a single dose, and the single dose sealed into a package. Such packages are particularly useful for dispersion in dry powder inhalers, as described in detail below. Alternatively, the powders may be packaged in multiple-dose containers.

The present invention further comprises dry powder compositions produced according to the methods described above, as well as unit dose and multidose packages of such dried powder compositions containing a therapeutically effective amount of the dry powder.

The present invention further provides methods for aerosolizing a dry powder composition comprising the steps of providing an amount of dry powder composition produced by any of the methods described above and subsequently dispersing the dry powder composition into a flowing gas stream.

DETAILED DESCRIPTION OF THE SPECIFIC EMBODIMENTS

Figure 1:
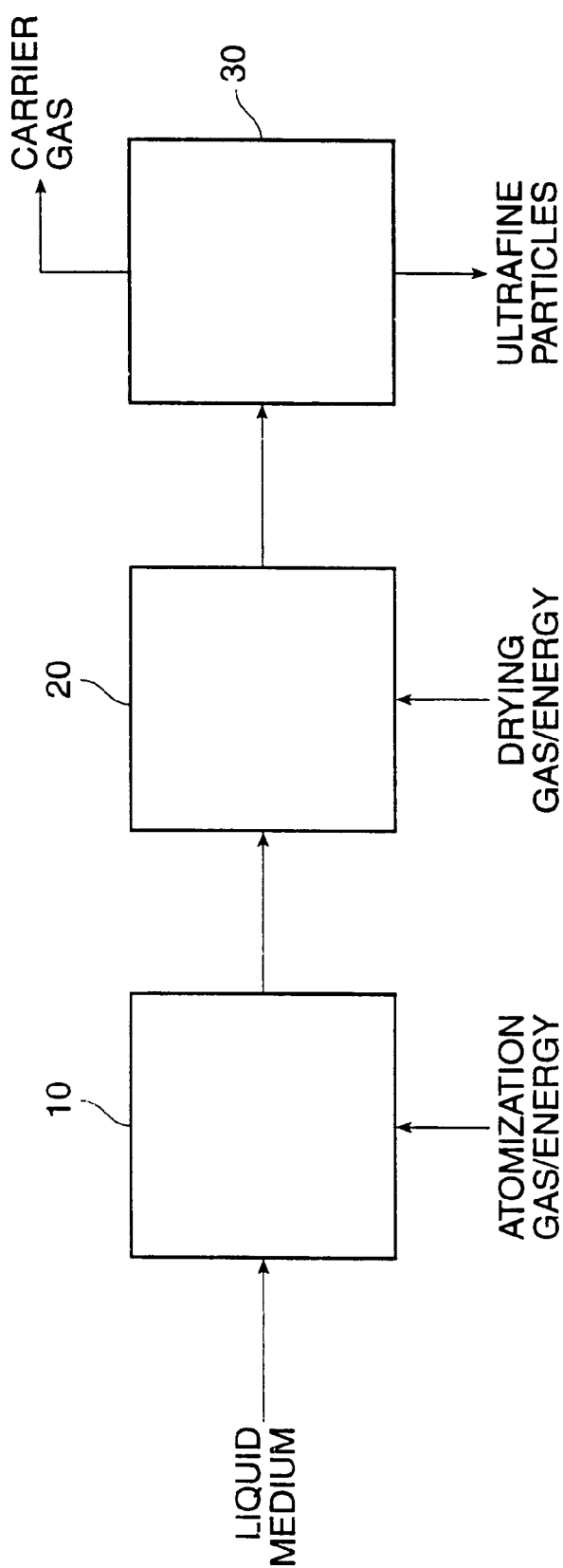
FIG. 1 is a block diagram illustrating a spray drying system suitable for performing the methods of the present invention.

The present invention relates to methods for preparing compositions comprising ultrafine dry powders having both hydrophobic and hydrophilic components. The methods are particularly suitable for producing ultrafine pharmaceutical dry powders where the hydrophobic component is a hydrophobic drug and the hydrophilic component is a hydrophilic excipient. The present invention, however, may find use for preparing a variety of other compositions including pharmaceutical compositions having hydrophilic drugs and hydrophobic excipients and compositions intended for non-pharmaceutical applications. The methods rely on spray drying liquid media in which the components are solubilized or suspended. In particular, the hydrophobic and hydrophilic components are solubilized in separate liquid media and the media are simultaneously spray dried through a common nozzle.

The term "hydrophobic component" refers to materials which are insoluble or sparingly or poorly soluble in water. As used herein, such compositions will have a solubility below 5 mg/ml, usually below 1 mg/ml. Exemplary hydrophobic drugs include certain steroids, such as budesonide, testosterone, progesterone, estrogen, flunisolide, triamcinolone, beclomethasone, betamethasone; dexamethasone, fluticasone, methylprednisolone, prednisone, hydrocortisone, and the like; certain peptides, such as cyclosporin cyclic peptide, retinoids, such as all-cis retinoic acid, 13-trans retinoic acid, and other vitamin A and beta carotene derivatives; vitamins D, E, and K and water insoluble precursors and derivatives thereof; prostagladins and leukotrienes and their activators and inhibitors including prostacyclin (epoprostanol), and prostaglandins $E_1$ $E_2$; tetrahydrocannabinol; lung surfactant lipids; lipid soluble antioxidants; hydrophobic antibiotics and chemotherapeutic drugs such as amphotericin B and adriamycin and the like.

By "hydrophilic component," it is meant that the component is highly soluble in water and frequently capable of swelling and formation of reversible gels. Typical aqueous solubilities of hydrophilic components will be greater than 5 mg/ml, usually greater than 50 mg/ml, often greater than 100 mg/ml and often much higher. In addition to their hydrophilic nature, the pharmaceutical excipients will generally be selected to provide stability, dispersibility, consistency and/or bulking characteristics to enhance the uniform pulmonary delivery of the dried powder composition to a patient. For pulmonary delivery, the excipients must be capable of being taken into the lungs with no significant adverse toxicological effects on the lungs. Exemplary hydrophilic excipients include carbohydrates and other materials selected from the group consisting of lactose, sodium citrate, mannitol, povidone, pectin, citric acid, sodium chloride, water soluble polymers, and the like. Particularly preferred are lactose, sodium chloride, sodium citrate, and citric acid which are generally accepted for pulmonary delivery in dry powder formulations.

The phrase "ultrafine dry powder" means a powder composition comprising a plurality of discrete, dry particles having the characteristics set forth below. In particular, the dry particles will have an average particle size below 10 μm, usually below 5 μm, preferably being in the range from 0.4 to 5 μm, more preferably from 0.4 to 4 μm. The average particle size of the powder will be measured as mass median diameter (MMD) by conventional techniques. A particular powder sizing technique uses a centrifugal sedimentary particle size analyzer (Horiba Capa 700). The powders will be capable of being readily dispersed in an inhalation device and subsequently inhaled by a patient so that the particles are able to penetrate into the alveolar regions of the lungs.

Of particular importance to the present invention, the ultrafine dry particle compositions produced by the method will have particle size distributions which enable them to target the alveolar region of the lung for pulmonary delivery of locally acting steroids, systemically acting proteins, and other biologically active materials that can be administered to or through the lungs. Such compositions advantageously may be incorporated into unit dosage and other forms without further size classification. Usually, the ultrafine dry powders will have a size distribution where at least 90% of the powder by weight will comprise particles having an average size in the range from 0.1 μm to 7 μm, with preferably at least 85% being in the range from 0.4 μm to 5 μm. Additionally, it is desirable that the particle size distribution avoid having an excess amount of particles with very small average diameters, i.e., below 0.4 μm.

The term "dry" means that the particles of the powder have a moisture and residual solvent content such that the powder is physically and chemically stable in storage at room temperature and is readily dispersible in an inhalation device to form an aerosol. Usually, the moisture and residual solvent content of the particles is below 10% by weight, usually being below 5% by weight, preferably being below 3% by weight, or lower. The moisture and residual solvent content will usually be controlled by the drying conditions, as described in more detail below. The term "dry" further means that the particles of the powder have a moisture and residual solvent content such that the powder is readily dispersible in an inhalation device to form an aerosol. In some cases, however, non-aqueous medium may be used for dispersing the components, in which case the aqueous content may approach zero.

The term "therapeutically effective amount" is the amount present in the composition that is needed to provide the desired level of hydrophobic drug in the subject to be treated to give the anticipated physiological response. This amount is determined for each drug on a case-by-case basis. The term "physiologically effective amount" is that amount delivered to a subject to give the desired palliative or curative effect. This amount is specific for each drug and its ultimate approval dosage level.

The therapeutically effective amount of hydrophobic drug will vary in the composition depending on the biological activity of the drug employed and the amount needed in a unit dosage form. Because the subject powders are dispersible, it is highly preferred that they be manufactured in a unit dosage form in a manner that allows for ready manipulation by the formulator and by the consumer. This generally means that a unit dosage will be between about 0.5 mg and 15 mg of total material in the dry powder composition, preferably between about 1 mg and 10 mg. Generally, the amount of hydrophobic drug in the composition will vary from about 0.01% w/w to about 95% w/w. Most preferably the composition will be about 0.05% w/w to about 25% w/w drug.

Referring now to FIG. 1, processes according to the present invention for preparing dispersible dry powders of hydrophobic and hydrophilic components comprise an atomization operation 10 which produces droplets of a liquid medium which are dried in a drying operation 20. Drying of the liquid droplets results in formation of the discrete particles which form the dry powder compositions which are then collected in a separation operation 30. Each of these unit operations will be described in greater detail below.

Figure 2:
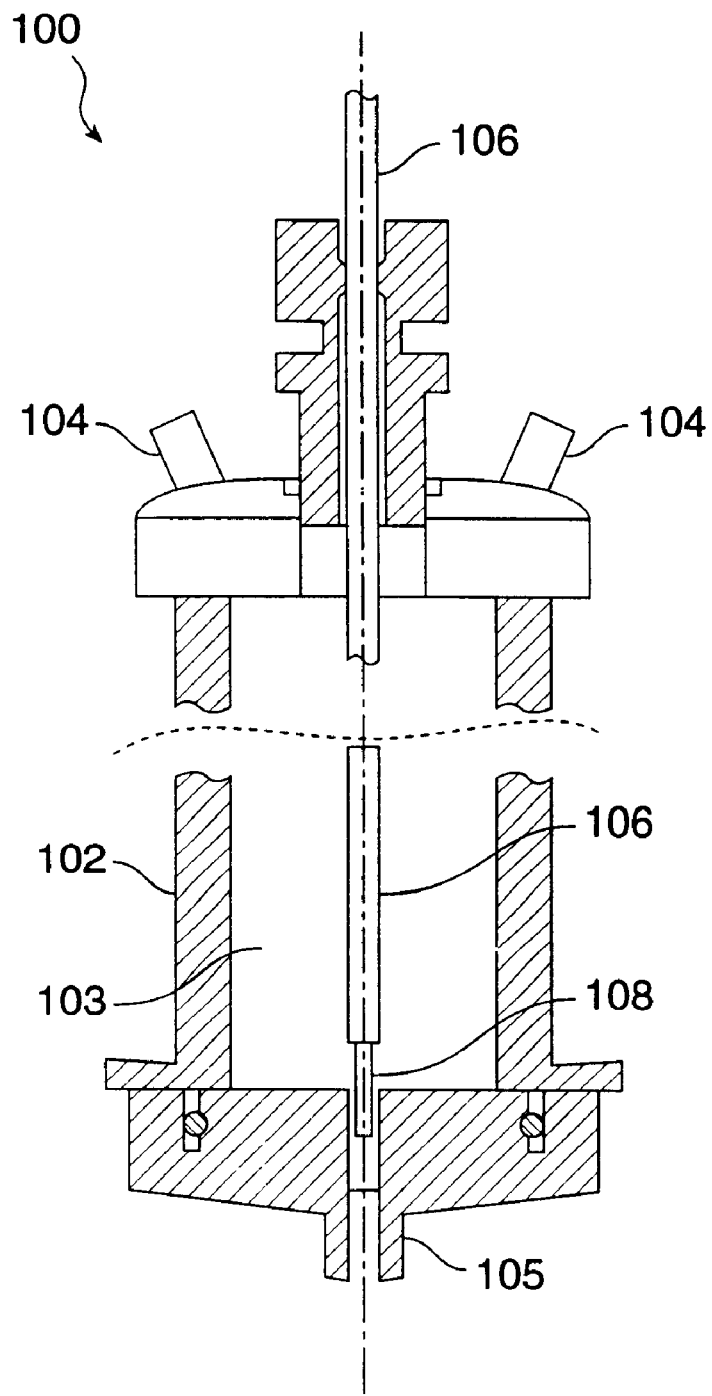
FIG. 2 illustrates a coaxial spray nozzle used in spray drying as described in the Experimental section.
Figure 3:
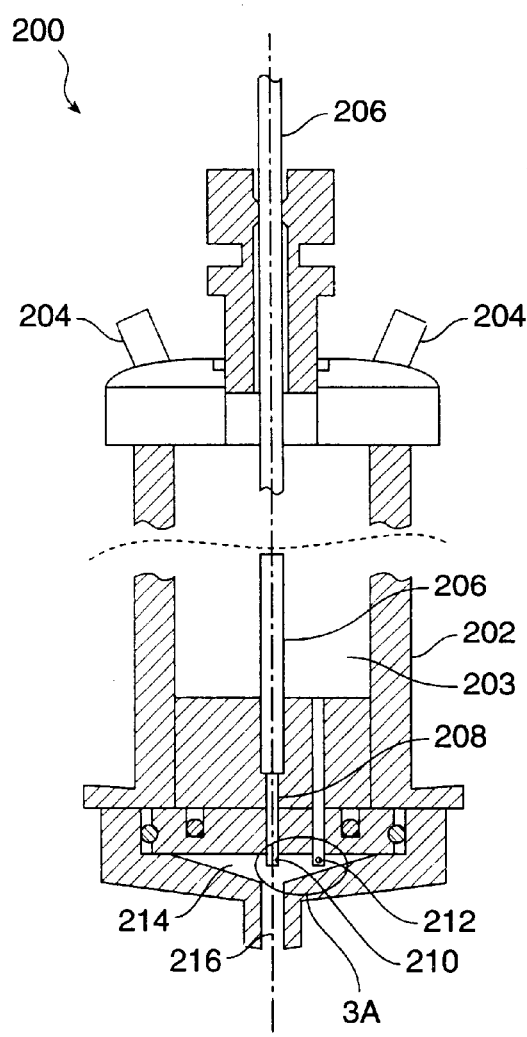
FIG. 3 illustrates a two-tube spray nozzle used in spray drying as described in the Experimental section.

The atomization process 10 may utilize any one of several forms of atomizers, so long as the atomizer is specially designed to deliver the liquid containing the hydrophobic components and the liquid containing the hydrophilic components separately to the lower portion of the atomizer, for which FIG. 2 and FIG. 3 serve as nonlimiting examples. The atomization process increases the surface area of the starting liquid. Due to atomization there is an increase in the surface energy of the liquid, the magnitude of which is directly proportional to the surface area increase. The source of this energy increase depends on the type of atomizer used. Any atomizer (centrifugal, sonic, pressure, two fluid) capable of producing droplets with a mass median diameter of less than about 20 $\mu$m could be used. Preferred for the present invention is the use of two fluid atomizers where the liquid medium is delivered through a nozzle concurrently with a high pressure gas stream. Particularly preferred is the use of two-fluid atomization nozzles as described in copending application Ser. No. 08/644,681, which is capable of producing droplets having a median diameter less than 20 $\mu$m.

The atomization gas will usually be nitrogen which has been filtered or otherwise cleaned to remove particulates and other contaminants. Alternatively, other gases, such as air may be used. The atomization gas will be pressurized for delivery through the atomization nozzle, typically to a pressure above 5 psig, preferably being above 10 psig. Although flow of the atomization gas is generally limited to sonic velocity, the higher delivery pressures result in an increased atomization gas density. Such increased gas density has been found to reduce the droplet size formed in the atomization operation. Smaller droplet sizes, in turn, result in smaller particle sizes. The atomization conditions, including atomization gas flow rate, atomization gas pressure, liquid flow rate, and the like, will be controlled to produce liquid droplets having an average diameter below 20 $\mu$m as measured by phase doppler velocimetry.

The drying operation 20 will be performed next to evaporate liquid from the droplets produced by the atomization operation 10. Usually, the drying will require introducing energy to the droplets, typically by mixing the droplets with a heated gas which causes evaporation of the water or other liquid medium. Preferably, the heated gas stream will flow concurrently with the atomized liquid, but it would also be possible to employ counter-current flow, cross-current flow, or other flow patterns.

The drying rate may be controlled based on a number of variables, including the droplet size distribution, the inlet temperature of the gas stream, the outlet temperature of the gas stream, the inlet temperature of the liquid droplets, and the manner in which the atomized spray and hot drying gas are mixed. Preferably, the drying gas stream will have an inlet temperature of at least 70° C. The outlet temperature will usually be at least about 40° C. The drying gas will usually be air or nitrogen which has been filtered or otherwise treated to remove particulates and other contaminants. The gas will be moved through the system using conventional blowers or compressors.

The separation operation 30 will be selected in order to achieve very high efficiency collection of the ultrafine particles produced by the drying operation 20. Conventional separation operations may be used, although in some cases they should be modified in order to assure collection of sub-micron particles. In an exemplary embodiment, separation is achieved using a filter medium such as a membrane medium (bag filter), a sintered metal fiber filter, or the like. Alternatively, and often preferably, separation may be achieved using cyclone separators, although it is usually desirable to provide for high energy separation in order to assure the efficient collection of sub-micron particles. The separation operation should achieve collection of at least 80% of all particles above 1 $\mu$m in average particle size, preferably being above 85%, more preferably being above 90%, and even more preferably being above 95%, in collection efficiency.

In some cases, a cyclone separator can be used to separate very fine particles, e.g. 0.1 $\mu$m, from the final collected particles. The cyclone operating parameters can be selected to provide an approximate cutoff where particles above about 0.1 $\mu$m are collected while particles below 0.1 $\mu$m are carried over in the overhead exhaust. The presence of particles below 0.1 $\mu$m in the pulmonary powder is undesirable since they will generally not deposit in the alveolar regions of the lungs, but instead will be exhaled.

The present invention relies on proper selection of the liquid medium or media for solubilizing the hydrophobic drug or other component and hydrophilic excipient or other component as well as on the manner of introducing the component to the spray dryer. In particular, the compositions are spray dried by forming separate solutions of the hydrophobic drug or other component and the hydrophilic excipient or other component. The separate solutions are then concurrently but separately introduced to the spray nozzle, typically by passing through a common spray nozzle or nozzles in the spray dryers described above. This method has the advantage that both the hydrophobic drug and the hydrophilic excipient may be easily dissolved since it is generally straight forward to select compatible solvents capable of fully dissolving only one of the components. By properly directing the two solutions through a nozzle, such as a coaxial nozzle, spray dried powders having uniform characteristics may be achieved. This approach has the additional advantage that it minimizes the amount of organic solvent required since only the hydrophobic drug or other component requires an organic solvent for dissolution. The hydrophilic excipient is dissolved in water.

An exemplary coaxial spray nozzle 100 is illustrated in FIG. 2 and includes a housing 102 defining a chamber 103.

A pair of inlets 104 are disposed at the top of the housing 102 for receiving the excipient solution (which is usually delivered at a higher volumetric flow rate than is the solution of the hydrophobic component). The excipient solution enters the chamber 103 at a pressure sufficient to achieve a desired flow rate through an outlet orifice 105 at the bottom of the housing 102. The hydrophobic component solution is fed through a feed tube 106 which usually terminates in a reduced diameter section 108 which is disposed coaxially within the orifice 105. The absolute and relative sizes of the orifice 105 and section 108 of feed tube 106 will depend on the total flow rates, operating pressures, and nature of materials being spray dried. A specific example is described in the Experimental section hereinafter.

Figure 3A:
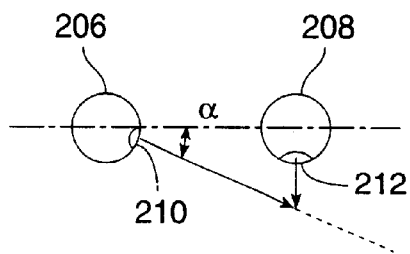
FIG. 3A is a detail cross-section view of region 3A in FIG. 3.

A second exemplary spray nozzle 200 is illustrated in FIGS. 3 and 3A. The nozzle 200 comprises a housing 202, inlets 204 and feed tube 206, generally similar to those described above for nozzle 100. Nozzle 200, however, is not coaxial and instead includes a second, parallel feed tube 208 which receives solution from chamber 203 defined within the housing 202. Both the feed tube 206 and feed tube 208 have outlet orifices 210 and 212, respectively, at their distal ends which direct the solution flow generally horizontally into a mixing chamber 214 disposed at the bottom of the housing 202. The mixing chamber is shown to have a conical geometry terminating at its bottom tip in outlet passage 216. The orifices 210 and 212 are preferably oriented as shown in FIG. 3A where the relative angle $\alpha$ is in the range from 5° to 25°, usually about 10°. Such an orifice arrangement results in a vortical mixing flow in the chamber 214 prior to ejection from the passage 216. A variety of other mixing chamber designs could also be utilized.

Once the dry powders have been prepared, they may be packaged in conventional ways. For pulmonary pharmaceutical applications, unit dosage forms may comprise a unit dosage receptacle containing a dry powder. The powder is placed within a suitable dosage receptacle in an amount sufficient to provide a subject with drug for a unit dosage treatment. The dosage receptacle is one that fits within a suitable inhalation device to allow for the aerosolization of the dry powder composition by dispersion into a gas stream to form an aerosol and then capturing the aerosol so produced in a chamber having a mouthpiece attached for subsequent inhalation by a subject in need of treatment. Such a dosage receptacle includes any container enclosing the composition known in the art such as gelatin or plastic capsules with a removable portion that allows a stream of gas (e.g., air) to be directed into the container to disperse the dry powder composition. Such containers are exemplified by those shown in U.S. Pat. No. 4,227,522 issued Oct. 14, 1980; U.S. Pat. No. 4,192,309 issued Mar. 11, 1980; and U.S. Pat. No. 4,105,027 issued Aug. 8, 1978. Suitable containers also include those used in conjunction with Glaxo's Ventolin Rotohaler® brand powder inhaler or Fison's Spinhaler® brand powder inhaler. Another suitable unit-dose container which provides a superior moisture barrier is formed from an aluminum foil plastic laminate. The pharmaceutical-based powder is filled by weight or by volume into the depression in the formable foil and hermetically sealed with a covering foil-plastic laminate. Such a container for use with a powder inhalation device is described in U.S. Pat. No. 4,778,054 and is used with Glaxo's Diskhaler® (U.S. Pat. Nos. 4,627,432; 4,811,731; and 5,035,237). Preferred dry powder inhalers are those described in U.S. patent application Ser. Nos. 08/309,691 and 08/487,184, assigned to the assignee of the present invention. The latter application has been published as WO 96/09085.

The following examples are offered by way of illustration, not by way of limitation.

EXPERIMENTAL

The following materials were used:
Budesonide (micronized to a median particle size of 1–2 $\mu$m; Steraloids)
Lactose monohydrate (NF grade; Foremost Ingredient Group)
Sodium Chloride (reagent grade from VWR and USP grade from EM Industries)
Deionized water
Ethanol, 200 proof (USP/NF; Spectrum Chemical Mfg. Corp.)
Acetone (for histology; EM Industries)

All batches were spray dried on Buchi 190 Mini Spray Dryers, with nozzles and cyclones that were designed to generate and catch very fine particles. A Buchi 190 Mini Spray Dryer was used that was modified so that it was supplied with nitrogen as the gas source and equipped with an oxygen sensor and other safety equipment to minimize the possibility of explosion. The solution feed rate was 5 ml/minute, inlet temperature was adjusted to obtain the outlet temperature noted in each example, and the top of the cyclone was jacketed and cooled to a temperature of about 30° C. for the examples in Table 1, but it was not cooled for the examples in Table 2. The drying nitrogen flow rate was about 18 SCFM, and the atomizing nitrogen was supplied at 0.5 to 1.5 SCFM. The powders were further dried in the collector for 5 minutes by maintaining approximately the outlet temperature and air volume after the feeding of the liquid formulation was completed.

Particle size was determined with a Horiba Particle Size Analyzer, model CAPA 700. Median particle size refers to the volume based particle size distribution of the prepared bulk powders determined via centrifugal sedimentation as follows. A sample of the powder was suspended in an appropriate liquid medium (one that minimizes solubilizing the particle), sonicated to break up the agglomerates, and then centrifuged. The median particle size was determined by measuring the sedimentation rate during centrifugation. This method provides the median size of the "primary" particle, that is, the size of the particles produced by the manufacturing process, plus potential modification during sample preparation. Because these formulations are composed of both water soluble and water insoluble materials, it is likely that the suspension step during sample preparation does to some extent solubilize part of the particle, and thereby modify the particle size that is determined. Therefore, the resultant particle sizes should be viewed as estimated values, rather than absolute values.

Moisture content was determined by the Karl-Fischer Reagent titrimetric method.

Delivered dose efficiency refers to a measure of the percentage of powder which is drawn out of a blister package and which exits the mouthpiece of an inhaler device as described in U.S. patent application Ser. No. 08/487,184. Delivered dose efficiency is a measure of efficiency for the powder package/device combination. The test was performed by connecting a vacuum system to the device mouthpiece. The vacuum system was set to be similar to a human inhalation with regard to volume and flow rate (1.2 liters total at 30 liters/minute). A blister package containing 0.5 to 10 mg of the formulation to be evaluated (5 mg of powder was used for the following examples) was loaded into a device which was held in a testing fixture. The device was pumped and fired, and the vacuum "inhalation" was switched on. The aerosol cloud was thus drawn out of the device chamber by the vacuum, and the powder was collected on a filter placed between the mouthpiece and the vacuum source. The weight of the powder collected on the filter was determined. Delivered dose efficiency was calculated by multiplying this weight by one hundred and dividing by the fill weight in the blister. A higher number was a better result than a lower number.

MMAD (mass median aerodynamic diameter) refers to a measure of the particle size of the aerosolized powder. MMAD was determined with an Andersen cascade impactor. In a cascade impactor the aerosolized powder (which was aerosolized using an inhaler device as described in U.S. patent application Ser. No. 08/487,184) enters the impactor via an air stream, and encounters a series of stages that separate particles by their aerodynamic diameter (the smallest particles pass farthest down the impactor). The amount of powder collected on each stage is determined gravimetrically, and the mass median aerodynamic diameter is then calculated.

Coaxial Nozzle System
Manufacturing Procedure

The budesonide was mixed in the organic solvent until all of the budesonide was completely dissolved to form a solution, with sonication if necessary. The excipient was mixed with the water until all of the excipient was completely dissolved to form a solution, with sonication, if necessary. The solutions were spray dried using a coaxial nozzle spray drying system having a nozzle as illustrated in FIG. 2 or FIG. 3. The FIG. 2 orifice 105 had a diameter of 1.0 mm and outlet tube section 108 had an outside diameter of 0.73 mm and an inside diameter of 0.6 mm. The FIG. 3 orifice 216 had a diameter of 1.0 mm and outlet orifices 210 and 212 had diameters of 0.15 mm.

The two solutions were fed to the nozzle at constant rates such that they both finished being fed to the nozzle at the same time.

Table 1 and Table 2 show the spray dryer atomization air pressure and outlet air temperature, the quantitative composition of example formulations, a description of the particle morphology, the moisture content, particle size, and delivered dose efficiency or MMAD of the resultant powders. Table 1 examples were spray dried using the nozzle illustrated in FIG. 2, whereas Table 2 examples were spray dried using the nozzle illustrated in FIG. 3.

TABLE 1

| Batch No., Formula No. (Spray Dryer Atomization Air Pressure/Outlet Air Temperature) | Quantitative Composition | | Particle Morphology | Moisture Content | Particle Size ($\mu$m) | Delivered Dose Efficiency |
|---|---|---|---|---|---|---|
| 329-44 B-13 (20PSI/76° C.) | Budesonide Ethanol Lactose DI water | 75 mg 25 ml 1425 mg 25 ml | Slightly wrinkled spheres | 0.76% | 2.11 | 42.0% (RSD = 25) |
| 329-47 B-14 (40PSI/77° C.) | Budesonide 9:1 Acetone:water Lactose DI water | 50 mg 1.25 ml 950 mg 98.75 ml | | 1.09% | 1.99 | 49.5% (RSD = 16) |

TABLE 2

| Batch No., Formula No., (Spray Drier Atomization Air Pressure/Outlet Air Temperature) | Quantitative Composition | | Particle morphology | Moisture Content | Particle Size ($\mu$m) | Powder MMAD ($\mu$m) |
|---|---|---|---|---|---|---|
| 446-63E-S B-38 (40PSI/77° C.) | Budesonide Ethanol Lactose NaCl DI Water | 187.5 mg 62.5 ml 656.25 mg 656.25 mg 12.5 ml | Smooth irregular spheres | 0.81% | 1.34 $\mu$m | 2.41 |
| 529-44B-S B-48 (30PSI/77° C.) | Budesonide Acetone Lactose NaCl DI Water | 165 mg 55 ml 577.5 mg 577.5 mg 11 ml | | 1.16% | 1.33 $\mu$m | 2.68 |

Although the foregoing invention has been described in some detail by way of illustration and example, for purposes of clarity of understanding, it will be obvious that certain changes and modifications may be practiced within the scope of the appended claims.

What is claimed is:

1. A method for preparing a dry powder composition, said method comprising:

preparing an aqueous solution of a hydrophilic component;

preparing an organic solution of a hydrophobic component in an organic solvent;

delivering the aqueous solution containing the hydrophilic component to an atomizer;

delivering the organic solution containing the hydrophobic component to the atomizer separately from the aqueous solution containing the hydrophilic component;

atomizing the two solutions together in the atomizer to produce droplets containing both components; and flowing the droplets of the aqueous solution and the organic solution in a heated gas stream to form dry particles comprising a mixture of the hydrophilic and hydrophobic components, said particles having a size distribution wherein at least 85% of the particles by weight comprise particles having an average size in the range from 0.4–5 µm.

2. A method as in claim 1, wherein the hydrophilic component has a concentration in the aqueous solution from 1 mg/ml to 100 mg/ml.

3. A method according to claim 2, wherein the hydrophobic component has a solubility of at least 0.01 mg/ml in the organic solvent.

4. A method as in claim 3, wherein the hydrophobic component has a concentration in the range from 0.01 mg/ml to 10 mg/ml in the organic solvent.

5. A method as in claim 1, wherein the organic solvent is selected from the group consisting of alcohols, ketones, ethers, aldehydes, hydrocarbons, and polar aprotic solvents and mixtures thereof.

6. A method as in claim 1, wherein the aqueous solution and the organic solution are atomized using a common nozzle.

7. A method as in claim 6, wherein the nozzle is a coaxial spray nozzle.

8. A method as in claim 1, wherein the hydrophobic component comprises a hydrophobic drug.

9. A method as in claim 8, wherein the hydrophobic drug is a steroid selected from the group consisting of budesonide, testosterone, progesterone, estrogen, flunisolide, triamcinolone, beclomethasone, betamethasone, dexamethasone, fluticasone, methylprednisolone, prednisone, hydrocortisone.

10. A method as in claim 8, wherein the hydrophobic drug comprises a peptide, a retinoid, vitamin D, vitamin E, vitamin K, precursors and derivatives of these vitamins, a prostaglandin, a leukotriene, tetrahydrocannabinol, lung surfactant lipid, an antioxidant, a hydrophobic antibiotic, and a chemotherapeutic drug.

11. A method as in claim 8, wherein the hydrophilic component comprises an excipient for the hydrophobic drug.

12. A method as in claim 11, wherein the hydrophilic excipient comprises a material selected from the group consisting of lactose, sodium citrate, mannitol, povidone, pectin, citric acid, sodium chloride, and mixtures thereof.

13. A method as in claim 1, further comprising screening the spray dried particles to disrupt agglomerates.

14. A method as in claim 1, further comprising:

measuring a single dosage of the dry powder; and sealing the single dosage in a package.

15. A dry powder composition prepared according to claim 1.

16. A unit dose of a dry powder composition comprising a unit dose receptacle having a therapeutically effective amount of a dry powder composition prepared according to claim 1.

17. A method for aerosolizing a dry powder composition said method comprising:

providing an amount of a dry powder composition prepared according to claim 1; and dispersing the dry powder composition into a flowing gas stream.

18. A method as in any one of claims 8–10 wherein the hydrophobic drug has a concentration in the range from 0.01 mg/ml to 10 mg/ml in the organic solvent.

* * * * *